United States Patent [19]

Frances et al.

[11] Patent Number: 5,084,543

[45] Date of Patent: Jan. 28, 1992

[54] TIN (IV) COMPOUNDS

[75] Inventors: Jean-Marc Frances, Villeurbanne; Verónique Gouron, Talence; Bernard Jousseaume; Michel Pereyre, both of Talence, all of France

[73] Assignee: Rhone-Poulenc Chimie, Courbevoie, France

[21] Appl. No.: 714,703

[22] Filed: Jun. 13, 1991

Related U.S. Application Data

[62] Division of Ser. No. 341,633, Apr. 21, 1989, Pat. No. 5,051,521.

[30]     Foreign Application Priority Data

Apr. 21, 1988 [FR] France ................. 88 05554

[51] Int. Cl.$^5$ ..................... C08G 18/08; C08G 18/24
[52] U.S. Cl. .................................. 528/58; 521/128
[58] Field of Search ................ 528/58; 521/128

[56]          References Cited

U.S. PATENT DOCUMENTS 3,206,489  9/1965  Stamm .
4,390,640  6/1983  Rasshofer et al. .
4,546,109 10/1985  Hubele et al. .
4,795,820  1/1989  Synoradzki et al. .

FOREIGN PATENT DOCUMENTS 1435756 6/1966 France .
966813 8/1964 United Kingdom .

Primary Examiner—Morton Foelak
Attorney, Agent, or Firm—Burns, Doane, Swecker & Mathis

[57]              ABSTRACT

Novel tetracoordinated tin (IV) compounds, well suited as latent catalysts for the preparation of polyurethanes or for the crosslinking of curable diorganopolysiloxanes (upon thermal decomposition thereof into diorganotin dicarboxylates or dialcoholates), have the general formula (1):

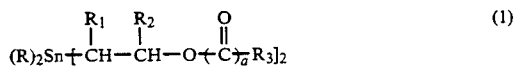

in which the radicals R, which may be the same or different, are each a linear or branched chain $C_1$-$C_{20}$ alkyl radical, a mononuclear aryl radical, or an aralkyl or alkaryl radical, the alkyl moieties of which having from 1 to 6 carbon atoms; the radicals $R_1$ and $R_2$, which may be the same or different, are each a hydrogen atom, a cyano radical, a $C_1$-$C_6$ alkyl radical, or an alkoxycarbonyl radical, the alkyl moiety of which having from 1 to 6 carbon atoms, with the proviso that $R_1$ and $R_2$ may together form a saturated hydrocarbon ring member having from 5 to 8 carbon atoms; the radical $R_3$ is a hydrogen atom, a linear or branched chain $C_1$-$C_{20}$ alkyl radical, a linear or branched chain $C_1$-$C_{20}$ alkoxy radical, a mononuclear aryl radical or a mononuclear aryloxy radical; and a is 0 or 1.

3 Claims, No Drawings

TIN (IV) COMPOUNDS

This application is a divisional, of application Ser. No. 07/341,633, filed Apr. 21, 1989, U.S. Pat. No. 5,051,521.

CROSS-REFERENCE TO COMPANION APPLICATION

Our copending application, Ser. No. 341,765 filed concurrently herewith and assigned to the assignee hereof.

BACKGROUND OF THE INVENTION

1. Field of the Invention

The present invention relates to novel tetra-coordinated tin compounds and to the use of such novel compounds as "latent" catalysts.

2. Description of the Prior Art

Numerous tin compounds have to date been proposed to this art as catalysts, in particular for:

(a) polyurethane synthesis: tin chelates (U.S. Pat. No. 3,055,845) and the products of reaction between a tin (IV) carboxylate and a sulfonyl isocyanate (DE-A-3,326,566 and EP-A-232,541), for example;

(b) the crosslinking of silicone polymers by a polycondensation reaction: dialkyltin dicarboxylates (Noll, *Chemistry and Technology of Silicones*, page 337, 2nd Edition, Academic Press (1968)), and dialkyltin bischelates (EP-A-147,323 and U.S. Pat. No. 4,517,337), for example.

SUMMARY OF THE INVENTION

A major object of the present invention is the provision of a novel class of tetracoordinated tin compounds that are inactive at ambient temperature (about 20° C.), particularly for those applications indicated above, but which are converted to active catalyst species at elevated temperatures. Such types of compounds are conventionally designated "latent" catalysts in this art.

Briefly, the present invention features novel latent catalyst compounds having the general formula:

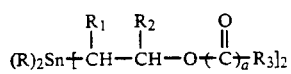
(1)

in which the R radicals, which may be the same or different, are linear or branched chain $C_1$–$C_{20}$ alkyl radicals, mononuclear aryl radicals, and aralkyl and alkaryl radicals, the alkyl moieties of which having from 1 to 6 carbon atoms; the $R_1$ and $R_2$ radicals, which may be the same or different, are hydrogen atoms, cyano radicals, $C_1$–$C_6$ alkyl radicals, and alkoxycarbonyl radicals, the alkyl moieties of which having from 1 to 6 carbon atoms, with the proviso that $R_1$ and $R_2$ may together form a saturated hydrocarbon ring having from 5 to 8 carbon atoms; the $R_3$ radical is a hydrogen atom, a linear or branched chain $C_1$–$C_{20}$ alkyl radical, a linear or branched chain $C_1$–$C_{20}$ alkoxy radical, a mononuclear aryl radical or a mononuclear aryloxy radical; and a is 0 or 1.

DETAILED DESCRIPTION OF THE PREFERRED EMBODIMENTS OF THE INVENTION

More particularly according to the present invention, the preferred R, $R_1$, $R_2$ and $R_3$ radicals and the number a are the following:

R: butyl, octyl and phenyl;
$R_1$: H;
$R_2$: H, methyl and cyano;
$R_3$: H, methyl, undecanoyl, 2-ethylpentyl, nonyl and ethoxy; and
a=1.

The preferred compounds of formula (1) are the following:

Bis(2-acetoxyethyl)dibutyltin, formula (1): R=butyl, $R_1=R_2=H$, $R_3=$methyl;

Bis(2-acetoxyethyl)dioctyltin, formula (1): R=octyl, $R_1=R_2=H$, $R_3=$methyl;

Bis(2-lauroyloxyethyl)dibutyltin, formula (1): R=butyl, $R_1=R_2=H$, $R_3=$undecanoyl;

Bis(2-lauroyloxyethyl)dioctyltin, formula (1): R=octyl, $R_1=R_2=H$, $R_3=$undecanoyl;

Bis[2-(2-ethylhexanoyloxy)ethyl]dibutyltin, formula (1): R=butyl, $R_1=R_2=H$, $R_3=$ethylpentyl;

Bis[2-(2-ethylhexanoyloxy)ethyl]dioctyltin, formula (1): R=octyl, $R_1=R_2=H$, $R_3=$2-ethylpentyl;

Bis(2-decanoyloxyethyl)dibutyltin, formula (1): R=butyl, $R_1=R_2=H$, $R_3=$nonyl (having a quaternary carbon in the 1-position;

Bis(2-acetoxy-2-methylethyl)dibutyltin, formula (1): R=butyl, $R_1=H$, $R_2=R_3=$methyl;

Bis(2-acetoxy-2-cyanoethyl)dibutyltin, formula (1): R=butyl, $R_1=H$, $R_2=CN$, $R_3=$methyl;

Bis(2-formyloxyethyl)dibutylin, formula (1): R=butyl, $R_1=R_2=R_3=H$;

Bis(2-ethoxycarbonyloxyethyl)dibutyltin, formula (1): R=butyl, $R_1=R_2=H$, $R_3=$ethoxy;

Bis(2-acetoxyethyl)diphenyltin, formula (1): R=phenyl, $R_1=R_2=H$, $R_3=$methyl;

Bis(2-lauroyloxyethyl)diphenyltin, formula (1): R=phenyl, $R_1=R_2=H$, $R_3=$undecanoyl.

The compounds of formula (1) may be prepared by addition reaction between a diorganotin dihydride of the formula (2):

(2)

in which the R radicals, which may be the same or different, are as defined above in respect of formula (1) and an enol carboxylate of the formula (3):

(3)

in which the $R_1$, $R_2$ and $R_3$ radicals and a are also as defined above in respect of formula (1).

The dihydrides of formula (2) are, for the most part, known compounds which are described in the literature. The novel such dihydrides may be prepared by reduction of the corresponding diorganotin dichloride with lithium aluminum hydride.

Another preparative process comprises reducing the corresponding diorganotin oxide with a polydiorganosiloxane bearing an SiH function, such as, for example, polyhydrogenated methylsiloxane having a trimethylsilyl group at each end of the polymer chain.

The carboxylates and alcoholates of formula (3) are for the most part also known and described in the literature.

Thus, for example, the vinyl carboxylates of formula:

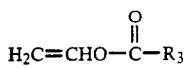

(formula (3): $R_1=R_2=H$) are prepared by transesterification of vinyl acetate with the acid $R_3COOH$, in an acid medium.

The enol carboxylates of the formula:

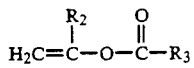

(formula (3): $R_1=H$, $R_3=CH_3$) are prepared by reaction of the ketone $H_3CCOR_2$ with isopropenyl acetate, in an acid medium.

The hydrostannation reaction between a compound of formula (2) and a compound of formula (3) is preferably carried out by reacting one mole of the compound of formula (2) with two moles of the compound of formula (3) at ambient temperature in an organic hydrocarbon solvent, such as cyclohexane. The reaction mixture is subjected to U.V. radiation (360 nm).

The hydrostannation reaction may also be carried out without a solvent in the presence of a free radical generator, such as, for example, in the presence of AIBN (azobisisobutyronitrile) at a temperature of 70° to 80° C.

The tin compounds of formula (1), which are generally liquid at ambient temperature, may be identified by the analytical techniques of I.R. (infra-red) spectroscopy and NMR (nuclear magnetic resonance $^{119}Sn$, $^{13}C$ and $^1H$), as well as by mass spectroscopy and measurement of the MOSSBAUER effect.

It would appear, however, that in the present state of the art of analytical techniques, the NMR $^{119}Sn$ analytical method, as described, in particular in the article by Peter J. Smith, "Chemical Shifts of $^{119}Sn$ Nuclei in Organotin Compounds", page 291 et seq., published in *Annual Reports on NMR Soectroscopy*, volume 8, Academic Press (1978), is a method which is itself sufficiently precise to characterize the various tin compounds present in a mixture, a reaction mixture in particular, and to enable the chemical formulae of most of these compounds to be established.

The fundamental parameter evaluated by NMR 119Sn is the chemical displacement value expressed in parts per million relative to a reference (generally tetramethyltin).

The chemical displacement value t is particularly sensitive to the electronegativity of the groupings borne by the tin and to the variation in the coordination number of the tin atom. Specific examples of the characterization of organotin derivatives using NMR $^{119}Sn$ are described, in particular, by A. G. Davies and P. J. Smith, *Comprehensive Organo-Metallic Chemistry*, 11, Tin, pages 523 to 529 and by J. Otera, *J. of Oroanomet. Chem.*, 221, pages 57–61 (1981).

The compounds of formula (1) are stable at ambient temperature and are inactive as catalysts for the preparation of polyurethanes and as catalysts for the hardening (curing) of organopolysiloxane compositions.

On the other hand, compounds of formula (1), when subjected to an elevated temperature, undergo thermal decomposition to well-known compounds, namely, the corresponding tin diorganodicarboxylates or tin diorganodialcoholates, simultaneously releasing the corresponding ethylenically unsaturated compound according to the following equation:

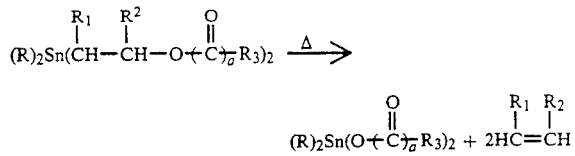

The thermal decomposition of the compounds of formula (1) takes place at a specific temperature for each of the compounds. This temperature generally ranges from 50° to 250° C.

When $R_3$ is an alkoxy radical and a=1, the resulting diorganotin dicarboxylate decomposes to a dialkoxydiorganotin with evolution of $CO_2$.

The tin diorganodicarboxylate or diorganodialcoholate thus released is then an active catalyst for the preparation of polyurethanes and the hardening of organopolysiloxane compositions.

The advantage of latent catalysts of the formula (1) is, hence, the possibility of mixing the starting materials with the latent catalyst in the absence of catalysis of the reaction, and initiating catalysis of the reaction by heating the mixture to the decomposition temperature of the latent catalyst.

This decomposition temperature may be lowered by addition of an effective amount of a nucleophilic agent selected, for example, from among water, a secondary organic amine, an organic alcohol, an organosilicon compound with a silanol function and an organic compound with a mercapto function (SH). By "effective amount" is intended from 0.001 mole to 10 moles or more of nucleophilic agent per mole of compound of formula (1).

Accordingly, the present invention also features a process for polyurethane preparation wherein an organic polyisocyanate is mixed at ambient temperature with an organic compound containing at least two groups with activated hydrogen atoms and a catalytically effective amount of a latent catalyst of formula (1), then heated to at least the thermal decomposition temperature of the latent catalyst.

The latent catalyst is used in a proportion of 0.001 to 6 parts, preferably 0.01 to 3 parts by weight, calculated as weight of the dry solids of the starting reactants.

The polyisocyanates and the organic compounds containing at least two groups having activated hydrogen atoms are well known to this art. They are described, for example, in U.S. Pat. No. 3,055,845 and EP-A-232,541.

The length of the shelf life of the reaction mixture is the same whether or not said mixture contains a latent catalyst of formula (1). This length of shelf life is at least six times higher than that observed for a reaction mixture containing an equimolar amount of the active catalyst corresponding to that obtained by decomposition of the latent catalyst of formula (1).

Catalysis is initiated as soon as the reaction mixture is heated to a temperature at least equal to the decomposition temperature of the latent catalyst. The reactivity observed is then similar to that obtained using an equimolar amount of the corresponding active catalyst.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Preparation and decomposition of bis(2-acetoxyethyl)dibutyltin (a) Preparation of dibutyltin dihydride:

$(C_4H_9)_2SnH_2$ 10.35 g of lithium aluminum hydride were placed in a 1-liter round-bottomed flask with three tubes and 250 ml of anhydrous ether were added drop-by-drop under nitrogen and with magnetic stirring. 52.1 g of dibutyltin dichloride, dissolved in 100 ml of anhydrous ether, were then added drop-by-drop. The reaction was exothermic. When addition was complete, the reaction mixture was heated to reflux for 2 hours, 30 min.

Then, 500 mg of hydroquinone and 100 ml of pentane were added successively. The mixture was then cooled to 0° C., then hydrolyzed slowly.

The organic phase was recovered and dried over magnesium sulfate. The solvents were eliminated under a vacuum of 2.7 kPa at ambient temperature.

The dibutyltin dihydride was distilled under a vacuum of 0.0013 pKa and a column head temperature of 35° C.

The reaction yielded 70% of dibutyltin dihydride: $(C_4H_9)_2SnH_2$, b.p.=35° C. under 0.0013 pKa.

Spectral characteristics:
NMR $^1$H (pure)δ(ppm)=4.6 (2 H, m); 1.65–0.9 (18 H, m)
NMR $^{119}$Sn ($C_6D_6$, $(CH_3)_4Sn$ internal) δ=204.0 ppm; $^1J(SnH)=1676$ Hz; $^2J(SnH)=56$ Hz
IR (film): ν(SnH)=1840 cm$^{-1}$ (F)

(b) Preparation of bis(2-acetoxyethyl)dibutyltin:

2.349 g (0.01 mole) of dibutyltin dihydride, 1.722 g (0.02 mole) of distilled vinyl acetate, and 2 g of anhydrous cyclohexane were placed in a Pyrex ® bowl thermostated at 25° C. The solution was exposed to ultraviolet radiation for 3 hours. The cyclohexane was then eliminated under vacuum at ambient temperature. The expected product was obtained pure in quantitative yield This operating procedure was the same in all cases where dibutyltin dihydride was added to an unsaturated compound. Only the temperature and the time of exposure may vary.

The product obtained had the following formula:

$(C_4H_9)_2Sn(CH_2CH_2OCOCH_3)_2$

Spectral characteristics:
NMR $^1$H (CCl$_4$, TMS int)δ(ppm)=4.7–3.75 (4 H, m); 1.95 (6 H, s); 1.7–0.9 (22 H, m)
NMR $^{119}$Sn ($C_6D_6$, $(CH_3)_4Sn$ internal)δ=−19.8 ppm;
IR (film): ν(CO)=1740 cm$^{-1}$ (F)

(c) Decomposition of bis(2-acetoxyethyl)dibutyltin 1.84 g of bis(2-acetoxyethyl)dibutyltin were placed in a test tube connecting with a water bowl. The tube was placed in an oil bath thermostated at 110° C. At the end of 2 hours, 30 min, 200 cc of gas were recovered and identified by IR spectroscopy; the spectrum of this gas was identical to that of ethylene (intense fine characteristic band at 950 cm$^{-1}$). The liquid obtained from the decomposition of the starting product (1.59 g) was distilled under a vacuum of 0.013 kPa at a column head temperature of 90° C. The product obtained was dibutyltin diacetate of the formula:

$(C_4H_9)_2Sn(OCOCH_3)_2$, b.p.=90° C. under 0.013 kPa

Spectral characteristics:
NMR $^1$H (CCl$_4$, TMS int)δ(ppm)=2.0 (6 H, s); 1.65–0.9 (18 H, m)
NMR $^{119}$Sn ($C_6D_6$, $(CH_3)_4Sn$ internal)δ=−156.3 ppm;
IR (film): ν(CO)=1605; 1570; 1425 cm$^{-1}$ (F).

EXAMPLE 2:

Preparation and decomoosition of bis(2-acetoxyethyl)-dioctyltin:

This preparation required the prior synthesis of dioctyltin dihydride $(C_8H_{17})_2SnH_2$.

(a) Preparation of dioctyltin dihydride:

The operating procedure followed was the same as that used in Example 1 for the synthesis of dibutyltin dihydride, except that dioctyltin dichloride was the starting material.

The product was obtained pure after bulb tube distillation, under a vacuum of $2.10^{-2}$ kPa at 90° C. (oven temperature).

Spectral characteristics:
NMR $^1$H (pure)δ(ppm)=4.6 (2 H, m); 1.65–0.9 (34 H, m).

(b) Preparation of bis(2-acetoxyethyl)dioctyltin:

The product was obtained in the same manner as its dibutyl series homolog: the bis(2-acetoxyethyl)dibutyltin of Example 1.

The product had the following formula:

$(C_8H_{17})_2Sn[(CH_2CH_2OCOCH_3)]_2$

Spectral characteristics:
NMR $^1$H (CCl$_4$, TMS int)δ(ppm)=4.65–3.7 (4 H, m); 1.95 (6 H, s); 1.65 - 0.9 (38 H, m)
NMR $^{119}$Sn ($C_6D_6$, $(CH_3)_4Sn$ internal)δ=−20.4 ppm;

(c) Decomposition of bis(2-acetoxyethyl)dioctyltin:

Decomposition of the pure product was complete after 3 hours at 110° C.

The product obtained was dioctyltin diacetate of the formula:

$(C_8H_{17})_2Sn(OCOCH_3)_2$

Spectral characteristics:
NMR $^1$H (CCl$_4$, TMS int)δ(ppm)=2.0–0.9 (40 H, m);
NMR $^{119}$Sn ($C_6D_6$, $(CH_3)_4Sn$ internal)δ=−156.8 ppm.

EXAMPLE 3

Preparation and decomposition of bis(2-lauroyloxyethyl)dibutyltin (a) Preparation of vinyl laurate:

51.5 g of vinyl acetate and 20 g (0.1 mole) of lauric acid were placed in a 100 ml round-bottomed flask with two tubes. The acid was dissolved by heating, 0.4 g of mercuric acetate was added in a stream of nitrogen. The mixture was thus stirred magnetically for 30 minutes at ambient temperature, under nitrogen. Two drops of sulfuric acid (95%) were then added and the reaction mixture heated to reflux for 3 hours. It was then permitted to return to ambient temperature, then 0.21 g of sodium acetate were added.

Excess vinyl acetate was recovered by distillation at atmospheric pressure.

The vinyl laurate was distilled under a vacuum of 0.013 kPa at 94° C. column head temperature.

The product was obtained in 70% yield. It had the following formula:

$H_2C=CHOCOC_{11}H_{23}$, b.p. = 94° C. under 0.013 kPa

Spectral characteristics:
NMR $^1H$ (CCl$_4$, TMS int)δ(ppm) = 7.2 (1 H, dd); 4.75 (1 H, dd); 4.45 (1H, dd); 2.3 (2H, t); 1.9–0.9 (21 H, m).

(b) Preparation of bis(2-lauroyloxyethyl)dibutyltin:

The operating procedure followed was the same as in Example 1. The vinyl acetate was replaced by 4.526 g (0.02 mole) of vinyl laurate. The solution was exposed to ultra-violet radiation for 4 hours.

The product, when was obtained quantitatively, had the following formula:

$(C_4H_9)_2Sn(CH_2CH_2OCOC_{11}H_{23})_2$

Spectral characteristics:
NMR $^1H$ (CCl$_4$, TMS int)δ(ppm) = 4.65–3.75 (4 H, m); 2.2 (4 H, t); 1.9–0.9 (4 H, m)
NMR $^{119}Sn$ (C$_6$D$_6$, (CH$_3$)$_4$Sn internal)δ = −20.0 ppm;
IR (film): ν(CO) = 1740 cm$^{-1}$ (F)

(c) Decomposition of bis(2-lauroyloxyethyl)dibutyltin:

Decomposition was carried out as in Example 1. At 140° C., it was complete after 2 hours, 30 min.

The decomposition product was identified as being dibutyltin dilaurate of the formula:

$(C_4H_9)_2Sn(OCOC_{11}H_{23})_2$

Spectral characteristics:
NMR $^1H$ (CCl$_4$, TMS int)δ(ppm) = 2.2 (4 H, t); 1.6–0.9 (60 H, m)
NMR $^{119}Sn$ (C$_6$D$_6$, (CH$_3$)$_4$Sn internal)δ = −152.5 ppm.

EXAMPLE 4

Preparation and decomposition of bis(2-laurolyloxyethyl)dioctyltin:

(a) Preparation of bis(2-lauroyloxyethyl)dioctyltin:

The product was obtained by hydrostannation of vinyl laurate The solution was exposed to ultraviolet radiation for 7 hours. The product had the following formula:

$(C_8H_{17})_2Sn(CH_2CH_2OCOC_{11}H_{23})_2$

Spectral characteristics:
NMR $^1H$ (CCl$_4$, TMS int)δ(ppm) = 4.6–3.9 (4 H, m); 2.4–0.9 (84 H, m)
NMR $^{119}Sn$ (C$_6$D$_6$, (CH$_3$)$_4$Sn internal)δ = −20.6 ppm;

(b) Decomposition of bis(2-lauroyloxyethyl)dioctyltin:

This was carried out under the same conditions as that of bis(2-lauroyloxyethyl)dibutyltin and yielded dioctyltin dilaurate:

$(C_8H_{17})_2Sn(OCOC_{11}H_{23})_2$

Spectral characteristics:
NMR $^1H$ (CCl$_4$, TMS int)δ(ppm) = 2.4–0.9 (80 H, m).

EXAMPLE 5

Preparation of bis2-(2-ethylhexanoyloxy)ethyl]dibutyltin:

(a) Preparation and decomposition of bis[2-(2-ethylhexanoyloxy)ethyl]dibutyltin:

2.349 g (0.01 mole) of dibutyltin dihydride, 3.405 g (0.02 mole) of distilled vinyl 2-ethylhexanoate and 2.5 g of anhydrous cyclohexane were placed in a Pyrex ® tube. Exposure to ultraviolet radiation was for 8 hours, 30 min, at 30–35° C. The solvent was eliminated under vacuum at ambient temperature.

The product of the reaction, which was obtained quantitatively, was the following:

$(C_4H_9)_2 Sn[CH_2CH_2OCOCH(C_2H_5)(C_4H_9)]_2$

Spectral characteristics:
NMR $^1H$ (CCl$_4$, TMS int)δ(ppm) = 4.7–4 (4 H, m); 2.4–0.9 (52 H, m)
NMR $^{119}Sn$ (C$_6$D$_6$, (CH$_3$)$_4$Sn internal)δ = −20.9 ppm;
IR (film): ν(CO) = 1735 cm$^{-1}$ (F)

(b) Decomposition of bis2-(2-ethylhexanoyloxy)ethyl]dibutyltin:

Decomposition was carried out as in Example 1. It was complete after 5 hours at 140° C. The product obtained was identified as being:

$(C_4H_9)_2Sn[OCOCH(C_2H_5)(C_4H_9)]_2$

Spectral characteristics:
NMR $^1H$ (CCl$_4$, TMS int)δ(ppm) = 2.5–0.9 (48 H, m)
NMR $^{119}Sn$ (C$_6$D$_6$, (CH$_3$)$_4$Sn internal)δ = −154.9 ppm.

EXAMPLE 6

Preparation and decomoosition of bis2-(2-ethylhexanoyloxy)-dioctyltin:

(a) Preparation of bis[2-(2-ethylhexanoyloxy)ethyl]-dioctyltin:

The addition of dioctyltin dihydride to vinyl 2-ethylhexanoate was carried out in the same manner as that of dibutyltin dihydride (Example 5).

It was complete after exposing the reaction mixture to ultraviolet radiation for 13 hours.

The product was obtained quantitatively and had the formula:

$(C_8H_{17})_2Sn[CH_2CH_2OCOCH(C_2H_5)(C_4H_9)]_2$

Spectral characteristics:
NMR $^1H$ (CCl$_4$, TMS int)δ(ppm) = 4.7–4.0 (4 H, m); 1.6–0.9 (68H, m)
NMR $^{119}Sn$ (C$_6$D$_6$, (CH$_3$)$_4$sn internal)δ = −21.7 ppm;

(b) Decomposition of bis2-(2-ethylhexanoyloxy)ethyl]dioctyltin:

This was carried out under the same conditions as the decomposition of the dibutyl homolog (Example 5).

The decomposition product had the following formula:

$(C_8H_{17})_2Sn[OCOCH(C_2H_5)(C_4H_9)]_2$

Spectral characteristics:
NMR $^{16}H$ (CCl$_4$, TMS int)δ(ppm)=2.5–0.9 (64 H, m);
NMR $^{119}Sn$ (C$_6$D$_6$, (CH$_3$)$_4$Sn internal)δ = −157.9 ppm.

EXAMPLE 7

Preparation and decomposition of bis(2-decanoyloxyethyl)dibutyltin (also known as bis(2-versatoyloxyethyl)dibutyltin)

(a) Preparation of vinyl versatate (also known as vinyl decanoate):

Versatic acid ® 10 (Shell) is a mixture of acids of molecular formula $C_{10}H_{20}O_2$, at least 98% of which contain a quaternary carbon atom in the alpha-position relative to the acid function. The radical R$_3$ in formula (1) is hence assimilable to a nonyl radical.

The operating procedure was the same as for the preparation of vinyl laurate. Vinyl versatate was obtained by distillation in 60% yield.

$H_2C=CHOCOC_9H_{19}$, b.p. 100° C. under 3.3 kPa.

Spectral characteristics:
NMR $^1H$ (CCl$_4$, TMS int)δ(ppm)=7.22 (1 H, dd); 4.78 (1 H, dd); 4.45 (1 H, dd); 2.0–0.8 (19 H, m).

(b) Preparation of bis(2-versatoyloxyethyl)dibutyltin:

The operating procedure of Example 1 was followed. The thermostated bowl was at 0° C. The solution was exposed to ultraviolet radiation for 2 hours. The expected product was obtained quantitatively; its formula was as follows:

$(C_4H_9)_2Sn(CH_2CH_2OCOC_9H_{19})_2$

Spectral characteristics:
NMR $^1H$ (CCl$_4$, TMS int)δ(ppm)=4.5–4.0 (4 H, m); 2.0–0.8 (60 H, m)
NMR $^{119}Sn$ (C$_6$D$_6$, (CH$_3$)$_4$Sn internal)δ = −22.3 ppm:
IR (film): ν(CO)=1730 cm$^{-1}$ (F)

(c) Decomposition of bis(2-versatoyloxyethyl)dibutyltin:

Decomposition was carried out as in Example 1. At 140° C., 65% of the product had disappeared after 4 hours (percentage estimated by NMR $^{119}Sn$). The decomposition product was dibutyltin diversatate:

$(C_4H_9)_2Sn(OCOC_9H_{19})_2$

Spectral characteristics:
NMR $^1H$ (CCl$_4$, TMS int)δ(ppm)=2.0–0.8 (56 H, m);
NMR $^{119}Sn$ (C$_6$D$_6$, (CH$_3$)$_4$Sn internal)δ = −162.6 ppm.

EXAMPLE 8

Preparation and decomposition of bis(2-acetoxy-2-methylethyl)dibutyltin:

(a) Preparation of bis(2-acetoxy-2-methylethyl)dibutyltin:

The operating procedure was the same as that in Example 7 for the addition to vinyl versatate; it was replaced here by 2.002 g (0.02 mole) of isopropenyl acetate. The reaction mixture was exposed to ultraviolet radiation for 3 hours, 30 min, at 0° C. The product, which was obtained quantitatively, had the following formula:

$(C_4H_9)_2Sn[CH_2CH(CH_3)OCOCH_3]_2$

Spectral characteristics:
NMR $^1H$ (CCl$_4$, TMS int)δ(ppm)=5.6–4.6 (2 H, m); 1.95 (6 H, s); 1.8–0.9 (28 H, m)
NMR $^{119}Sn$ (C$_6$D$_6$, (CH$_3$)$_4$Sn internal)δ = −24.9 ppm;

(b) Decomposition of bis(2-acetoxy-2-methylethyl)dibutyltin:

The pure product was heated in a test tube to 80° C. Decomposition was complete after one quarter of an hour. Dibutyltin diacetate was obtained pure. Its characteristics are reported at the end of Example 1.

EXAMPLE 9

Preparation and decomoosition of bis(2-acetoxy-2-cyanoethyl)dibutyltin

Addition of dibutyltin dihydride to 1-cyanovinyl acetate was conducted following the operating procedure of Example 1. Exposure to ultraviolet radiation was for 5 hours. The product obtained was identified as being bis(2-acetoxy-2-cyanoethyl)dibutyltin, of the formula:

$(C_4H_9)_2Sn[CH_2CH(CN)OCOCH_3]_2$

Spectral characteristics:
NMR $^1H$ (CCl$_4$, TMS int)δ(ppm)=5.4 (2 H, t); 2.1 (6 H, s); 1.65–0.9 (22 H, m)
NMR $^{119}Sn$ (C$_6$D$_6$, (CH$_3$)$_4$Sn internal)δ = −22.6 ppm;

(b) Decomposition of bis(2-acetoxy-2-cyanoethyl)dibutyltin:

Decomposition was carried out as in Example 1 at 110° C; a mixture of dibutyltin diacetate and acrylonitrile was obtained after 2 hours, without any trace of the starting material.

Spectral characteristics of acrylonitrile: $CH_2=CH$ CN
NMR $^1H$ (CCl$_4$, TMS int)δ(ppm)=6.4–5.4
For those of $(C_4H_9)_2Sn(OCOCH_3)_2$: see Example 1.

EXAMPLE 10

Preparation and decomposition of bis(2-formyloxyethyl)dibutyltin:

(a) Preparation of vinyl formate:

The operating procedure followed was the same as that in Example 3 for the preparation of vinyl laurate. Distillation was carried out in a Cadiot apparatus (50 cm column with revolving band). The product obtained had the following formula:

$H_2C=CHOCOH$, b.p.=45° C. under 100 kPa

Spectral characteristics:
NMR $^1H$ (CCl$_4$, TMS int)δ(ppm)=8.05 (1 H, s); 7.32 (1 H, dd); 4.95 (1 H, dd); 4.65 (1 H, dd).

(b) Preparation and decomposition of bis(2-formyloxyethyl)dibutyltin:

Addition of dibutyltin dihydride to vinyl formate was carried out in a Pyrex ® tube at 30–35° C. following the operating procedure of Example 5. The product was not isolated because it decomposed as it was formed.

Only the spectral characteristics of dibutyltin diformate are reported here: $(C_4H_9)_2Sn(OCOH)_2$ NMR $^1H$ ($C_6$, $D_6$, TMS int)$\delta$(ppm) = 8.25 (2 H, s); 1.8–0.9 (18 H, m);

NMR $^{119}Sn$ ($C_6D_6$, $(CH_3)_4Sn$ internal)$\delta$ = −102.5 ppm.

EXAMPLE 11

(a) Preparation and decomposition of bis(2-ethoxycarbonyloxyethyl)dibutyltin (a) Preparation of ethyl vinyl carbonate:

6.14 g of ethanol (0.13 mole), 10.5 g of pyridine and 80 ml of pentane were placed in a 250 cc round-bottomed flask with two tubes. A solution of 14.2 g (0.13 mole) of vinyl chloroformate in 50 ml of pentant was added dropwise at ambient temperature under magnetic stirring. The resulting pyridinium hydrochloride precipitated. Stirring was maintained for 3 hours after the addition was complete. The reaction mixture was then taken up in water, which dissolved the precipitate.

The organic phase was recovered, washed with a saturated aqueous solution of sodium chloride until the wash water was neutral and dried over magnesium sulfate. The solvent was eliminated by distillation. The ethyl vinyl carbonate was then distilled at 115° C. under 100 kPa.

The product obtained had the following formula:

$H_2C=CHOCOOCH_2CH_3$ b.p. = 115–116° C. under 100 kPa

Spectral characteristics:
NMR $^1H$ ($CCl_4$, TMS int)$\delta$(ppm) = 6.95 (1 H, dd); 4.75 (1 H, dd); 4.42 (1 H, dd); 4.15 (2 H, g); 1.3 (3 H, t).

(b) Synthesis of bis(2-ethoxycarbonyloxyethyl)dibutyltin:

The operating procedure was the same as that of Example 1. Exposure time was 2 hours.

The expected product was obtained quantitatively:

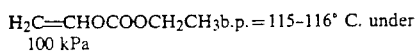
$(C_4H_9)_2Sn(CH_2CH_2OCOOCH_2CH_3)_2$

Spectral characteristics:
NMR $^1H$ ($CCl_4$, TMS int)$\delta$(ppm) = 4.3 (4 H, t); 4.1 (4 H, q); 1.5–0.9 (28 H, m).

(c) Decomposition of bis(2-ethoxycarbonyloxyethyl)-dibutyltin:

This took place rapidly at 20° C. and yielded diethoxydibutyltin: $(C_4H_9)_2Sn(OCH_2CH_3)_2$.

Spectral characteristics:
NMR $^1H$ ($CCl_4$, TMS int)$\delta$(ppm) = 3.7 (4 H, q); 1.5–0.9 (24 H, m);
NMR $^{119}Sn$ ($C_6D_6$, $(CH_3)_4Sn$ internal)$\delta$ = −154.5 ppm.

EXAMPLE 12

Preparation and decomposition of bis(2-acetoxyethyl)diphenyltin (a) Preparation of diohenyltin dihydride:

The operating procedure followed was the same as that used in Example 1 for the synthesis of dibutyltin dihydride. The product was unstable; it required distillation in clean glass apparatus (ungreased connections). This was carried out in a bulb tube, under a vacuum of 0.27 kpa, at 100–110° C. (oven temperature).

(b) Preparation of bis(2-acetoxyethyl)diphenyltin:

Stoichiometric amounts of diphenyltin dihydride and vinyl acetate were placed in a Pyrex ® tube containing anhydrous cyclohexane. The reaction mixture was exposed to ultraviolet radiation for 1 hour at 30° C. The solvent was then eliminated at ambient temperature under vacuum. The product was obtained quantitatively and had the following formula:

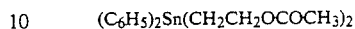
$(C_6H_5)_2Sn(CH_2CH_2OCOCH_3)_2$

Spectral characteristics:
NMR $^1H$ ($CCl_4$, TMS int)$\delta$(ppm) = 7.6–6.9 (10 H, m); 4.75–3.7 (4 H, m); 1.75–0.9 (10 H, m).

(c) Decomposition of bis(2-acetoxyethyl)diohenyltin:

Decomposition of the pure product was complete after 1 hour at 150° C., and yielded diphenyltin diacetate of the formula:

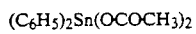
$(C_6H_5)_2Sn(OCOCH_3)_2$

Spectral characteristics:
NMR $^1H$ ($CCl_4$, TMS int) t (ppm) = 7.9–7.0 (10 H, m); 1.8 (4 H, m); (6 H, s).

EXAMPLE 13

Preparation and decomposition of bis(2-lauroyloxyethyl)diphenyltin:

(a) Preparation of bis(2-lauroyloxyethyldiohenyltin:

The product was obtained under the same conditions as previously in Example 12. The product had the following formula:

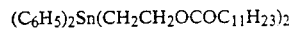
$(C_6H_5)_2Sn(CH_2CH_2OCOC_{11}H_{23})_2$

Spectral characteristics:
NMR $^1H$ ($CCl_4$, TMS int) t (ppm) = 7.5–6.9 (10 H, m); 4.75–3.7 (4 H, m); 2.2–0.75 (50 H, m).

b) Decomposition of bis(2-lauroyloxyethyl)diphenyltin:

After 1 hour at 150° C., the product had disappeared; diphenyltin dilaurate was obtained:

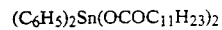
$(C_6H_5)_2Sn(OCOC_{11}H_{23})_2$

Spectral characteristics:
NMR $^1H$ ($CCl_4$, TMS int) t (ppm) = 7.75–7.0 (10 H, m); 2.2–0.75 (46 H, m).

EXAMPLE 14:

(a) Preparation of bis(2-ethoxyethyl)dibutyltin:

The operating procedure followed was the same as in Example 1 except that the vinyl acetate was replaced by (0.02 mole) vinyl ethylate.

The solution was placed in a sealed tube, under nitrogen atmosphere in the presence of azobisisobutyronitrile (0.01 mmole) and stirred magnetically for 5 hours at 80° C.

The product obtained in largest quantity had the formula:

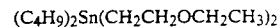
$(C_4H_9)_2Sn(CH_2CH_2OCH_2CH_3)_2$

Spectral characteristics:
NMH $^1H$ ($CCl_4$, TMS int)$\delta$(ppm) = 3.5 ppm (8 H, m); 0.9–1.6 ppm (28 H, m);
NMR $^{119}Sn\delta$(ppm) = −17.7 ppm.

(b) Decomposition of bis(2-ethoxyethyl)dibutyltin:
Decomposition of the pure product was complete after 2 hours, 30 min, at 180° C. and yielded diethoxydibutyltin of the formula:

$(C_4H_9)_2Sn(OCH_2CH_3)_2$

Spectral characteristics:
NMR $^1H$ (CCl$_4$, TMS int)$\delta$(ppm)=3.7 (4 H, q); 1.5–0.9 (24 H, m);
NMR $^{119}Sn$ (C$_6$D$_6$, (CH$_3$)$_4$Sn internal)$\delta$=−154.5 ppm.

EXAMPLES 15 to 17 and COMPARATIVE EXAMPLES 18 to 21

Preparation of a reaction mass by mixture of a diol, a diisocyanate and an organotin compound

REACTANTS:

(i) The diol used was a mixture of 1,4-butanediol and a polyether of molecular weight 1,000, each end of the polymer chains of which has OH functions;
(ii) the diisocyanate used was IPDI: 3-isocyanatomethyl-3,5,5-trimethylcyclohexyl isocyanate of the formula:

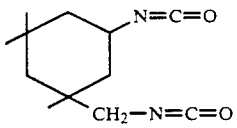

(iii) the organotin compound was used in proportions of 0.03 parts of compound per 100 parts by weight (of dry solids) of diol and IPDI.

Operating procedure:

The following materials were placed in a vacuum flask:
(1) 5.26 g of polyether;
(2) 0.8 g of 1,4-butanediol.
The mixture was degassed and 1 ml of a solution of 0.15 g of organotin compound in 50 ml of anhydrous ether was added.
The solvent was evaporated under vacuum and 3.94 g of IPDI were added.
The final reaction mixture was degassed for 2 minutes.
Examples 15 to 21 used the same reaction mixture. The nature of the organotin compound in each of these examples was as follows:

EXAMPLE 15

Bis(2-acetoxyethyl)dibutyltin prepared in Example 1.

EXAMPLE 16

Bis(2-lauroyloxyethyl)dibutyltin prepared in Example 3.

EXAMPLE 17

Bis[2-(2-ethylhexanoyloxy)ethyl]dibutyltin prepared in Example 5.

EXAMPLE 18

Control with no organotin compound.

EXAMPLE 19

Dibutyltin diacetate.

EXAMPLE 20

Dibutyltin dilaurate.

EXAMPLE 21

Dibutyltin di(2-ethylhexanoate).

The reaction mixture of each example was divided into three parts.
The first part was used to determine gel time (length of shelf life) at ambient temperature (20° C.) and the second and third to determine crosslinking time at 100° C. and 140° C., respectively.
The results obtained are reported in the following table.

TABLE

| EXAMPLES | 15 | 16 | 17 | 18 | 19 | 20 | 21 |
|---|---|---|---|---|---|---|---|
| Length of shelf life (at 20° C.) | 8 h | 8 h | 7 h, 30 min | 8 h | 55 min | 1 h, 40 min | 1 h, 50 min |
| Crosslinking time at 100° C. | 8 min | 8 min, 30 s | 8 min | — | 4 min | 5 min | 5 min |
| Crosslinking time at 140° C. | 5 min | 5 min | 5 min, 30 s | — | 3 min | 3 min | 3 min |

The above table shows that the reaction masses have the same shelf life with a latent catalyst of the invention (Examples 15 to 17) as with no organotin compound (control Example 18).
The crosslinking time of the reaction masses is slightly longer, but of the same order of magnitude when a latent catalyst is used as when its corresponding thermal degradation product is used directly (Examples 19 to 21).
While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A process for the preparation of a polyurethane, comprising reacting an organic diisocyanate with an organic compound containing at least two groups having active hydrogen atoms, in the presence of a catalytically effective amount of a tetracoordinated tin (IV) compound having the general formula (1):

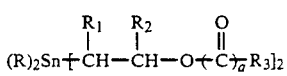

in which the radicals R, which are the same or different, are each a linear or branched chain $C_1$–$C_{20}$ alkyl radical, a mononuclear aryl radical, or an aralkyl or alkaryl radical, the alkyl moieties of which having from 1 to 6 carbon atoms; the radicals $R_1$ and $R_2$, which may be the same or different, are each a hydrogen atom, a cyano radical, a $C_1$–$C_6$ alkyl radical, or an alkoxycarbonyl radical, the alkyl moiety of which having from 1 to 6 carbon atoms, with the proviso that $R_1$ and $R_2$ may together form a saturated hydrocarbon ring member having from 5 to 8 carbon atoms; the radical $R_3$ is a hydrogen atom, a linear or branched chain $C_1$–$C_{20}$ alkyl radical, a linear or branched chain $C_1$–$C_{20}$ alkoxly radical, a mononuclear aryl radical or a mononuclear aryloxy radical; and a is 0 or 1, and said reaction being carried out at a temperature at least equal to the decomposition temperature of said tin (IV) compound.

2. The process as defined in claim 1 wherein said tin (IV) compound is bis(2-acetoxyethyl)dibutyltin.

3. The process as defined by claim 1 wherein said tin (IV) compound is bis[2-(2-ethylhexanoyloxy)ethyl]-dibutyltin.

* * * * *